United States Patent [19]
Medoff

[11] Patent Number: 5,941,878
[45] Date of Patent: Aug. 24, 1999

[54] IMPLANTABLE, SURGICAL BUTTRESSING DEVICE

[76] Inventor: Robert J. Medoff, 159 Ku'ukama St., Kailua, Hi. 96734

[21] Appl. No.: 09/005,138

[22] Filed: Jan. 9, 1998

Related U.S. Application Data

[63] Continuation-in-part of application No. 08/590,899, Jan. 24, 1996, Pat. No. 5,709,682.

[51] Int. Cl.$^6$ .................................................... A61B 17/58
[52] U.S. Cl. ................................ 606/60; 606/72; 606/151
[58] Field of Search ................................ 606/60, 64, 72, 606/73, 151, 75, 219, 220, 69

[56] References Cited

U.S. PATENT DOCUMENTS

| | | | |
|---|---|---|---|
| 3,486,500 | 12/1969 | Ball et al. | 606/105 |
| 4,169,470 | 10/1979 | Ender et al. | 606/62 |
| 4,838,254 | 6/1989 | Gauthier | 606/75 |
| 5,013,314 | 5/1991 | Firica et al. | 606/72 |
| 5,190,544 | 3/1993 | Chapman et al. | 606/69 |
| 5,197,966 | 3/1993 | Sommerkemp | 606/69 |
| 5,449,359 | 9/1995 | Groiso | 606/75 |
| 5,487,741 | 1/1996 | Marayuma et al. | 606/69 |

FOREIGN PATENT DOCUMENTS

| | | | |
|---|---|---|---|
| 491382 | 2/1975 | U.S.S.R. | 606/70 |
| 1512584 | 10/1989 | U.S.S.R. | 606/69 |
| 1648427 | 5/1991 | U.S.S.R. | 606/105 |
| 2290473 | 1/1996 | United Kingdom . | |

*Primary Examiner*—Michael Buiz
*Attorney, Agent, or Firm*—Ladas & Parry

[57] ABSTRACT

An implantable surgical device for fixation of one or more bone fragments or grafts to an adjacent stable bone. The device is formed by a U-shaped wire having a U bend portion and two legs extending from the U bend portion, the device being secured near the U bend portion by a fixation device including a washer and a bone screw to a stable bone. The distal ends of the legs are formed with pointed projections or with bends providing projections extending out of the plane of the U-shaped wire to penetrate the surface of the bone fragment or graft and provide translational constraint of the fragment or graft.

9 Claims, 13 Drawing Sheets

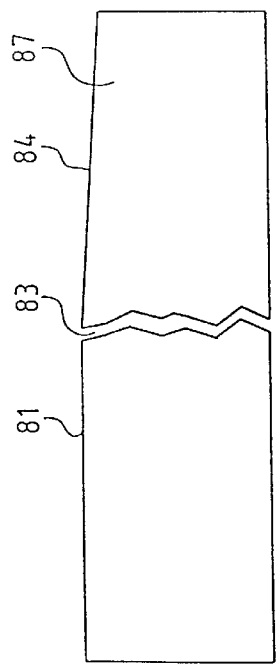
Fig.15a
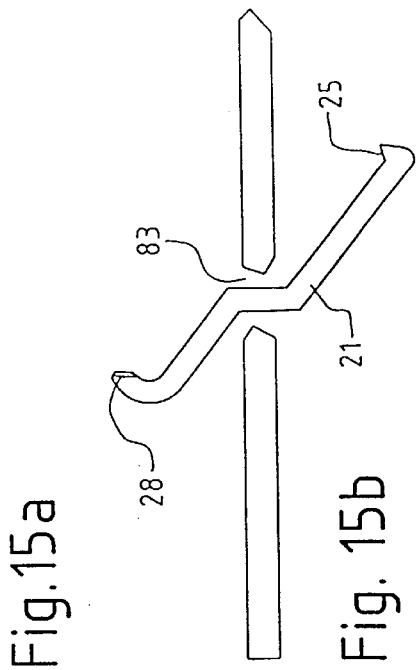
Fig. 15b
Fig. 15c
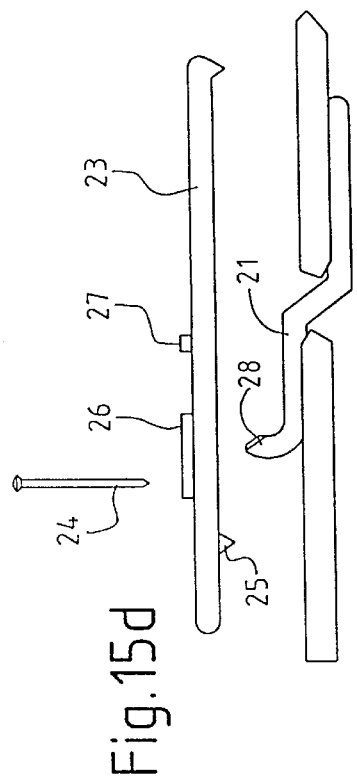
Fig.15d
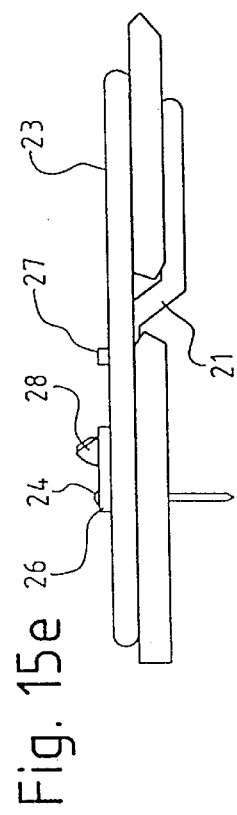
Fig. 15e
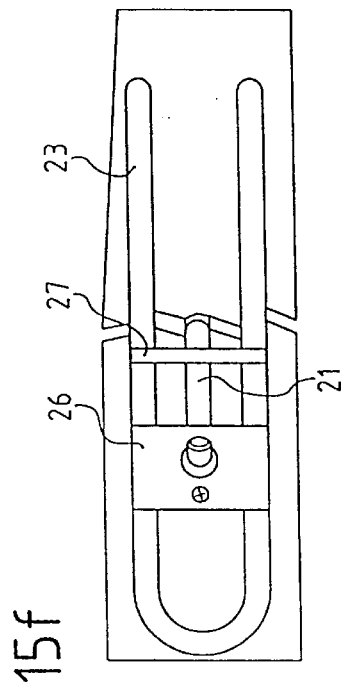
Fig. 15f

IMPLANTABLE, SURGICAL BUTTRESSING DEVICE

CROSS-RELATED APPLICATION

This application is a continuation-in-part of Ser. No. 08/590,899 filed Jan. 24, 1996, now U.S. Pat. No. 5,709,682.

FIELD OF THE INVENTION

The invention relates to an implantable, surgical buttressing device especially for fixation of bone fragments and grafts to a stable bone.

BACKGROUND AND PRIOR ART

A fracture near a joint has always been difficult to treat, as the ideal treatment is to achieve rigid fixation of the fracture fragments while allowing nearly immediate motion of the joint.

In order to simplify the description, the present invention is described in connection with fractures about the wrist, and particularly those fractures collectively referred to as Colles' fractures. A person skilled in the art will appreciate that the invention is also applicable in fixation of other bones. Possible other bones include, but are not limited to, bones of the elbow, knee, and ankle. This may require a change of the shape of the device for each specific area, but the same principles are used irrespective of the site of the fracture. However, the major use of the invention is thought to be for fixation of Colles' fractures.

Treatment of distal radius fractures has been a problem, both because of the frequency of the injury as well as the difficulty in treating them. The goal of treatment is to restore joint congruity and anatomy, minimize the risk of arthritis, and maximize joint mobility. However, although these injuries are almost always treated on an outpatient basis, they typically result in stiffness, arthritis, and diminished function.

There are today essentially four general groups of options available for the treatment of Colles' fractures: (1) closed reduction and casting, (2) external fixation, (3) open reduction and internal fixation, and (4) percutaneous pinning and/or limited open pinning. Each method has its limitations; each has its benefits.

Closed reduction simply involves setting or aligning the broken bone manually and applying a cast to the arm. This treatment avoids any trauma associated with surgery, and is relatively inexpensive. However, it has several disadvantages. It involves cast immobilization until healing of the bone fragments occurs; this frequently results in considerable stiffness. This stiffness is not just confined to the wrist and forearm. Immobilizing the arm in an elderly individual often results in considerable stiffness to the fingers, elbow, and shoulder as well. In addition, this technique is very limited in its ability to hold all but the simplest, most stable fracture patterns in proper alignment. Unstable fractures commonly redisplace during healing, which can lead to arthritis and pain.

External fixation involves the application of relatively large diameter pins inserted into the finger metacarpal bones of the fingers and into the radius above the fracture. These pin clusters are then connected with a bar or frame, essentially "bypassing" the fracture site. Typically, two pins are placed in the hand, and two pins in the radius. The frame may distract the wrist as well, in order to assist with fracture reduction, by using the soft tissue sleeve around the fracture to help squeeze the fragments into position. Although external fixation has its proponents, it has its problems. The wrist and hand are rigidly held by the frame, and the pins through the skin tend to irritate the tendons and cause scarring. These problems together cause considerable stiffness in both the wrist and the fingers. Frequently the functional loss of grip can be more disabling than the fracture. Pin site infections may also occur and compromise results. External fixation may not achieve an anatomic reduction of the fragments. Currently, external fixation is used for more severely comminuted, fragmented fractures.

Open reduction involves making an incision over the wrist reducing the fragments, and applying plates, screws, and pins as needed. For the Colles' fracture open reduction and internal fixation is seldom used, for several reasons. First, the trauma associated with the dissection and exposure can lead to scarring of the tendons, loss of gliding, and stiffness. Second, the dissection can compromise the blood supply to the fragments, which can result in delayed unions and occasionally non-unions. Third, the fragments tend to be small and osteoporotic; drilling holes and placing screws frequently fragments these pieces further, making anatomic reduction even more difficult. Fourth, most of the fragments and displacement in the typical Colles' fracture are on the dorsal side, and the irregularity of the radius in this area together with the many tendons found near the bone on this side makes it undesirable to place plates and screws dorsally. Finally, these fractures are often comprised of numerous small pieces which must be reduced in a jigsaw puzzle type of arrangement, not easily treated by plate and screw fixation.

Percutaneous pinning involves the placement of small stiff pins, also called K-wires, across fragments of the fracture. The pins may be inserted directly through the skin while imaging the fracture with a fluoroscopy unit. Limited small incisions may also be used. Typically, pin diameters range from 0.010" to 0.250", with the 0.045" and 0.054" pin sizes commonly used in the USA. Pinning has certain advantages. Using a percutaneous or limited open technique to pin fragments allows the fracture to be internally fixed. This provides some additional stability internally which is not available when the fracture is treated with a cast alone. The fragments in these fractures tend to be small and the bone osteoporotic. As a result, pins are more appropriate as a type of fixation than screws in this setting. A small diameter pin has less chance of weakening the fragment and comminuting it further compared with screw holes that are made with even small diameter bone screws.

Pinning, however, has its problems. In order to secure a fragment, there must be a stable bone nearby for securing the pin. Frequently, the only stable piece of bone is the proximal fragment, which may be some distance and at a difficult angle away from the fragment to be pinned. Since the pins have a small diameter, they are likely to bend or displace if the stable piece of bone is relatively far from the fracture fragment. This reduces the ability of the pin to maintain the position of the fragment and, in turn, impedes the process of healing.

In certain cases multiple fragments are put together like stacking cards, by fixing one fragment to a stable proximal piece, and then pinning a second fragment to the first, which is assumed to be stabilized by the first pin. This frequently makes the entire assembly dependent upon one or two pins which may engage the stable proximal cortex at some distance from the fracture fragment. Such situations are often unstable.

Because pins have a strong tendency to bend and displace due to motion of the joint, pins are hardly ever used without casting. This means that the patient is still subjected to the common complications of stiffness and loss of function that is associated with the cast.

The applicant's patent application SE 9500285-3 describes a method for using pins together with a pin plate for fixation and stabilization of the pin or pins penetrating the bone fragments. This method overcomes many of the problems involved with previous methods of treating many types of Colles' fractures when using pins. It achieves the objective of providing rigid fixation of the fracture fragments while allowing immediate mobility of the joint.

However, pinning the fracture is not suitable or even possible for all types of Colles' fractures. Often, in order to use pins, there needs to be a stable piece of bone for attaching the pin located on the opposite cortex of the fragment from where the pin is inserted. If the only nearby solid piece of bone is located on the cortex adjacent to the fracture fragment, pinning becomes a geometric impossibility. An example of such a situation occurs when a Colles' fracture results in a dorsal ulnar fragment and a fracture of the opposite volar radial surface. In these cases, there is no stable cortex available for angles of pin insertion which are technically feasible.

In some cases, the hole itself created by placing a pin or screw to secure a small fragment would significantly weaken the fragment and compromise fixation and stability. In such situations, these devices may further comminute the fracture.

In other situations, fractures of the distal radius result in multiple pieces, creating dorsal, palmar, and intra-articular fragments. In such cases, it is difficult to support the various fragments in the appropriate anatomic position simply by pinning. Moreover, fragments which are completely intra-articular are not well treated with simple pinning, since leaving a pin through an articular surface can destroy the adjacent articular surface, resulting in severe arthritis.

SUMMARY OF THE INVENTION

An object of the invention is to provide implantable means for fixation of bone fragments and grafts which overcomes the problems associated with the known art.

The means according to the invention has two basic functions; namely, a buttress function and a clamp function. Either function or both can be employed dependent upon the particular embodiment selected to treat the fracture.

One example of the buttress function is to assist in the reduction of a completely intra-articular fragment. Since this fragment is entirely within the joint, it is not possible to place a fixation device directly through it without compromising the articulating surfaces. One solution for stabilizing these types of fragments is to pack bone graft behind the fragment, in order to force it up against the opposite side of the joint. This requires bone from a bone bank, or removal of bone from a different site of the same patient. Both of these alternatives add additional risk to the patient. A buttress pin according to the invention provides a more stable means of buttressing such a fragment, without the risks of bone graft.

The basic design of the buttress pin is to provide a buttress on the intraosseous surface of a bone fragment to constrain it from moving in a particular direction. In one embodiment, the buttress pin has a section which is passed through an opening in the cortex (either through the fracture or through drilled holes) and which can then be positioned to support an intra-articular fragment from the desired direction.

The clamp function is useful to stabilize a fragment when a transosseous pin or screw is not indicated. It combines an intraosseous and extraosseous buttress adjacent to a common bone cortex. In cases where there is no opposite stable cortex or in cases where any additional holes in the fragment would cause further comminution, a small fragment clamp could be used. A small fragment clamp according to the invention allows a small fragment to be captured and secured to the cortex of bone adjacent to the fragment.

The basic design of the small fragment clamp is to provide a form for clamping a small fragment on its upper and lower surfaces which can then be secured to an adjacent portion of stable bone. In its preferred embodiments, the small fragment clamp is comprised of two main sections. One section is used to engage and buttress the fragment from the intraosseous surface of the cortical bone while the other section is used to engage the extraosseous surface. The sections are "pinched" together to grab the fragment securely and then are fastened to the adjacent cortex of stable bone.

In this way the small fragment clamp allows small fragments to be grasped, positioned, buttressed and secured in an anatomic position. Since the fragment is held in place by the gripping action of the "fingers" of the device, it is not applicable for fractures with large forces across the fracture site, as in weight bearing joints. However, for fractures of the distal radius, it is ideal for assisting in fixation that may be rigid enough to avoid the use of a cast.

The invention also contemplates the use of a U-shape wire serving as an implantable surgical buttressing means for fixation of one or more bone fragments or grafts to an adjacent stable bone.

BRIEF DESCRIPTION OF THE DRAWINGS

The present invention will now be described in greater detail hereinbelow, with the aid, of embodiments shown in the drawings. In the accompanying drawings:

FIGS. 15a–15f show application of the device of FIGS. 12–14 on a fracture;

DETAILED DESCRIPTION OF PREFERRED EMBODIMENTS

Figure 1:
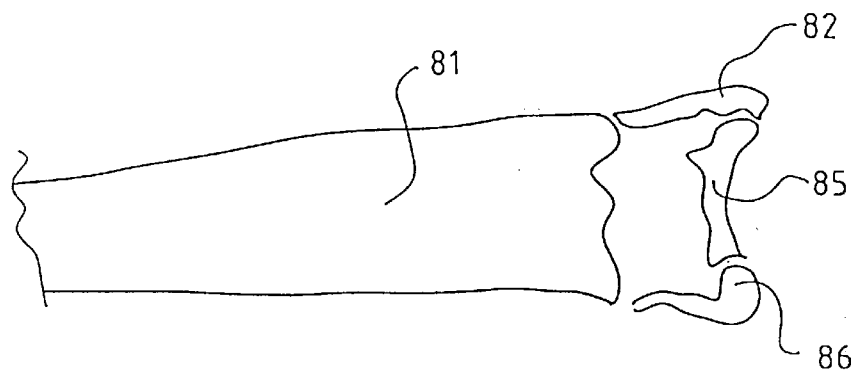
FIG. 1 shows one typical fragmentation for Colles' fractures.

In FIG. 1 a typical fragmentation of the distal radius 81 is shown. In this case three fragments 82, 85, 86 are formed. A dorsal ulnar fragment 82, an intra-articular fragment 85 and a palmar lip fragment 86. This fragmentation pattern is used for descriptive purposes only, in order to explain the invention.

For the fixation of the intra-articular fragment 85 a buttress according to the invention is used. In the embodiment shown in FIGS. 2 to 4 there is only one major part, namely a first part 41 or buttress pin. The distal end of the first part 41 is formed as a buttress 49. In this embodiment the first part 41 is U-shaped in top view, and is furnished with pointed projections 45 for engagement with bone cortex. The buttress pin is secured to the stable bone with a bone screw 44 cooperating with a washer 46.

Buttressing of an intra-articular fragment 85 from the intraosseous side is not limited to use in the distal radius. Other joints, such as the elbow, knee, and ankle, are suitable for this type of device.

Figure 2:
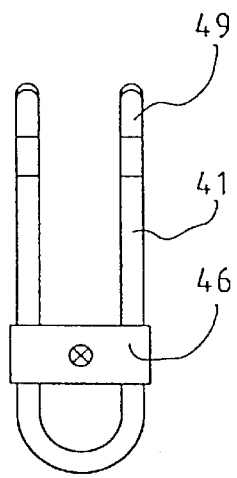
FIGS. 2–4 are top, side and end views, respectively, of a first embodiment of the invention.
Figure 3:
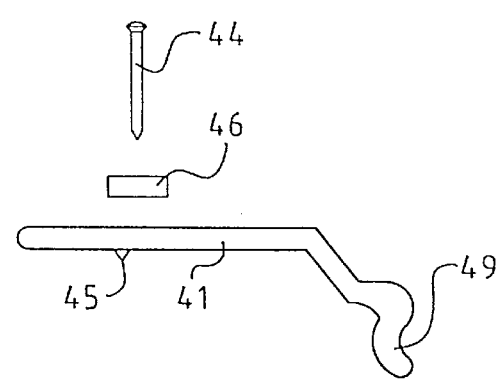
Figure 4:
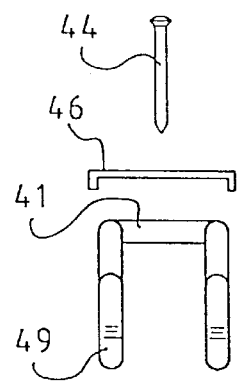
Figure 5:
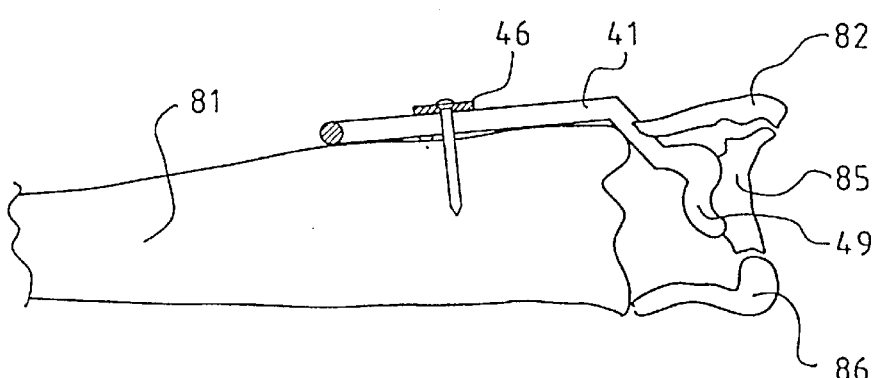
FIG. 5 shows in sectional view application of the device of FIGS. 2–4 on a fracture.

FIG. 5 shows application of the buttress pin of FIGS. 2 to 4 on a fracture. The buttress pin is driven up behind the fragment 85 to push it against the adjacent cortex. In this position the device is secured to the stable bone 81 with the bone screw 44 cooperating with the washer 46. The pointed projections 45 help to give a stable fixation. This device 41 is stiff enough to allow the fragment 85 to be maintained in position against the opposite side of the joint. On the other hand, the device 41 is flexible enough to allow it to be removed after fracture healing without significant disruption of bone. Thus, this device 41 buttresses from the intraosseous side of the fragment. All existing buttress plates place the buttress on the superficial surface of the bone.

It will be additionally noted that the device 41 provides an intraosseous buttress to the cortical fragment 82 as shown in FIG. 5. This provides a stable floor against which this cortical fragment may abut, providing additional stability to this fragment. It is readily apparent that the device is capable of being used as an intraosseous buttress for either an intra-articular fragment, an unstable cortical fragment, or a combination of the two.

For the fixation of the dorsal ulnar fragment 82 a small fragment clamp according to the invention is used. The basic design of the small fragment clamp is to provide a form of sandwiching effect for fixation of the fragment 82. This effect combines an intraosseous buttress with an extraosseous buttress in order to further constrain movement of the fragment, without the need of invasively drilling through the fragment. The fragment clamp is made of two parts. The first part grabs the fragment 82 from the undersurface and the second part grips the upper surface of the fragment 82.

Figure 6:
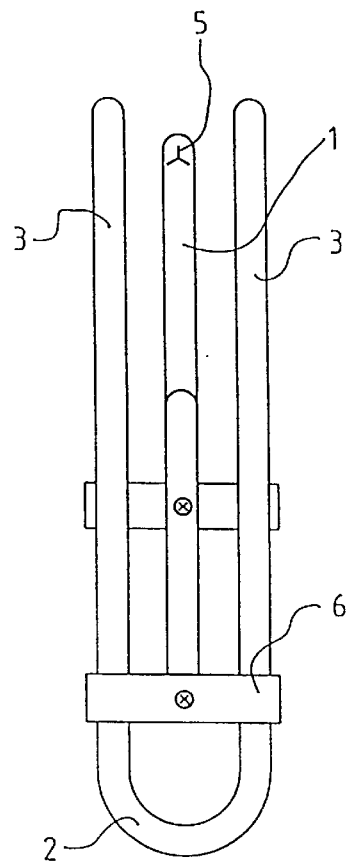
FIGS. 6–8 are top, side and end views, respectively, of a second embodiment of the invention.
Figure 7:
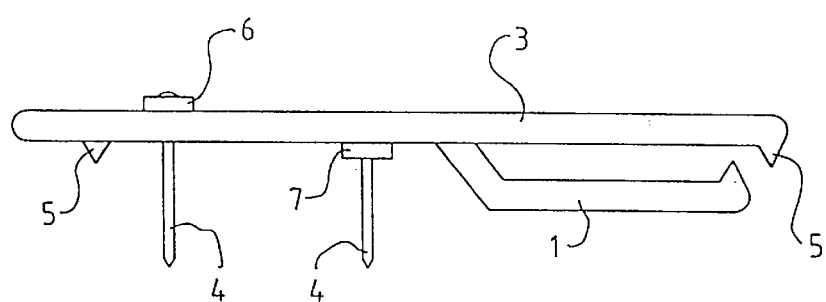
Figure 8:
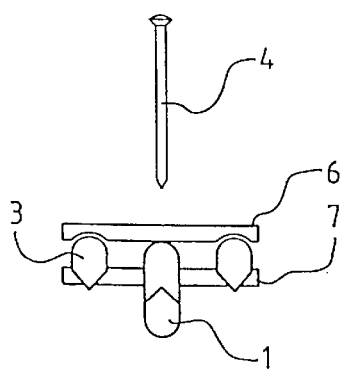

In a first embodiment of the fragment clamp shown in FIGS. 6 to 8 the first part 1 has two cross tabs 6, 7. The distal tab 7 acts as a fulcrum or axis of rotation of the first part 1 on the second part 2. This prevents the first part 1 from lifting up out of the second part 2.

Both the first part 1 and the second part 2 have pointed projections 5 for engagement with bone cortex.

In this embodiment the first part 1 is linear in top view and is bent in side view, the forward bent section being intended to grip and buttress on the intraosseous side of the fragment 82. The second part 2 has a general U-shape with two legs 3. To secure the components to the stable bone 81, bone screws 4 are applied through holes in the tabs 6, 7.

This fixation also secures the components 1, 2 to each other. Since the first and second parts 1, 2 are not directly coupled, the surgeon may slide the first part 1 distally or proximally depending upon the size of the fragment intended to be fixed. Once the device is applied, however, the two parts 1 and 2 no longer move relative to each other. The pressure of the cross tabs 6, 7 on the second part 2 essentially joins the first and second parts 1, 2 together.

Figure 9:
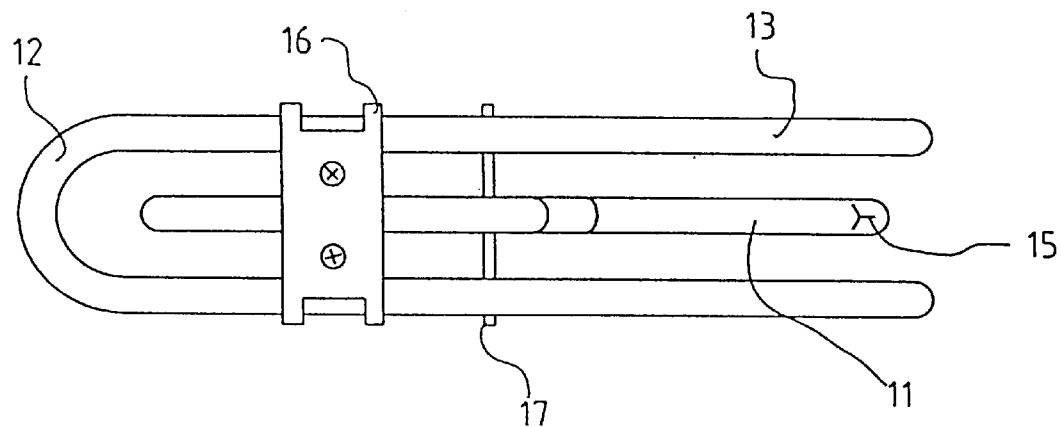
FIGS. 9–11 are top, side and end views, respectively, of a third embodiment of the invention.
Figure 10:
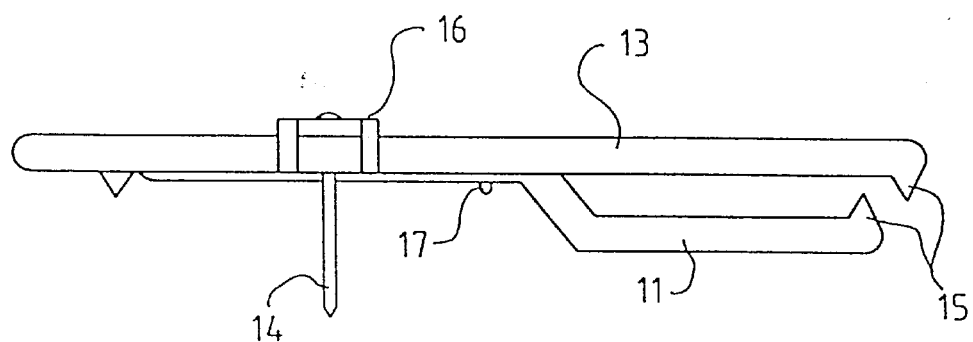
Figure 11:
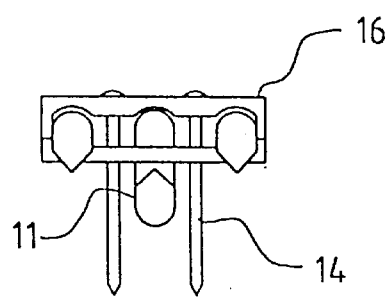

In a second embodiment of the fragment clamp shown in FIGS. 9 to 11 the first part 11 has a cross pin 17, acting as a fulcrum for rotation of the first part. As in the first embodiment the first part 11 is linear having a bent section in side view, and the second part 12 has a general U-shape with two legs 13 in top view and is linear in side view.

Fixation for the second embodiment is accomplished with bone screws 14 passing through a matching washer 16. The washer 16 locks the first and second parts 11, 12 to each other as well as to the bone 81.

Both the first and second parts 11, 12 have pointed projections 15 for engagement with bone cortex.

Figure 12:
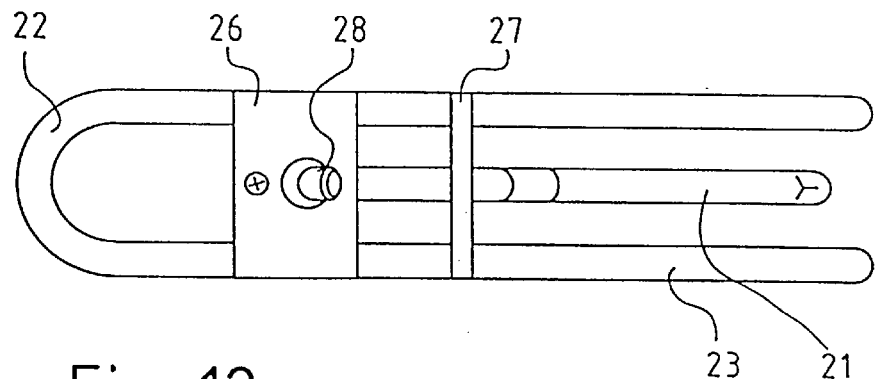
FIGS. 12–14 are top, side and end views, respectively, of a fourth embodiment of the invention.
Figure 13:
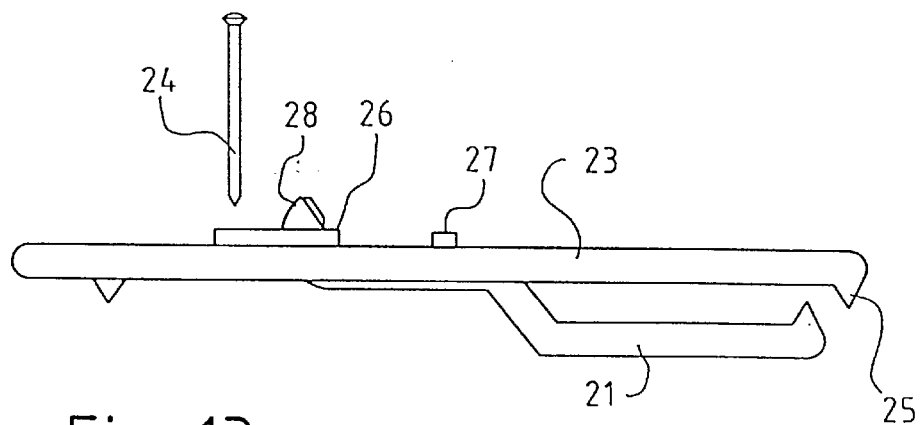
Figure 14:
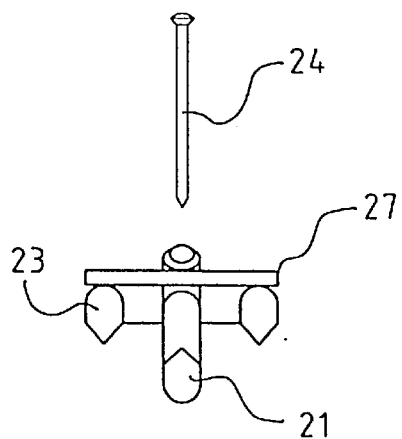

A third embodiment of the fragment clamp is shown in FIGS. 12 to 14. In this embodiment the first and second parts 21, 22 have the same general shape as in the above embodiments. Furthermore they are furnished with pointed projections 25 for engagement with bone cortex.

The second part 22 has a cross pin 27 and a cross bar 26 bridging the legs 23 of the second part 22. The cross bar 26 is furnished with an opening for receiving a bone screw 24 securing the device to the stable bone 81. The cross bar 26 is also used to capture an upwardly directed hook 28 on the first part 21. In this embodiment the device has been limited to two components.

FIGS. 15a to 15f show one way to secure the device according to the third embodiment to a stable bone 81. The first part 21 is first placed by having it pass through the fracture 83. If necessary a notch 84 is removed or a transosseous hole is made to allow the passage of the first part 21. When the first part has been placed with the pointed projection 25 in engagement with and buttressing the intraosseous side of an unstable fragment 87, the second part 22 is placed on top of the first part 21 in a position where the hook 28 of the first part 21 is captured by the cross bar 26. Finally a bone screw 24 passing through an opening in the cross bar 26 secures the device to the stable bone. As the screw 24 is fastened the projections 25 of the first and second parts 21, 22 will engage the bone cortex and stabilize the position of the device. Thus, the bone fragment 87 is sandwiched between the first and second parts 21, 22 and is secured to the stable bone 81.

In some cases a hole is made in the stable bone at some distance from the actual fracture site. The first part is inserted through said hole. The rest of the device is secured as described above. Sometimes a special tap or clamping device is used to temporarily fix the first part to the stable bone. The unstable fragment is then placed on top of the intraosseous arms of the first part and the second part is thereafter placed on top. Finally the tap is replaced with a screw and washer.

Figure 16:
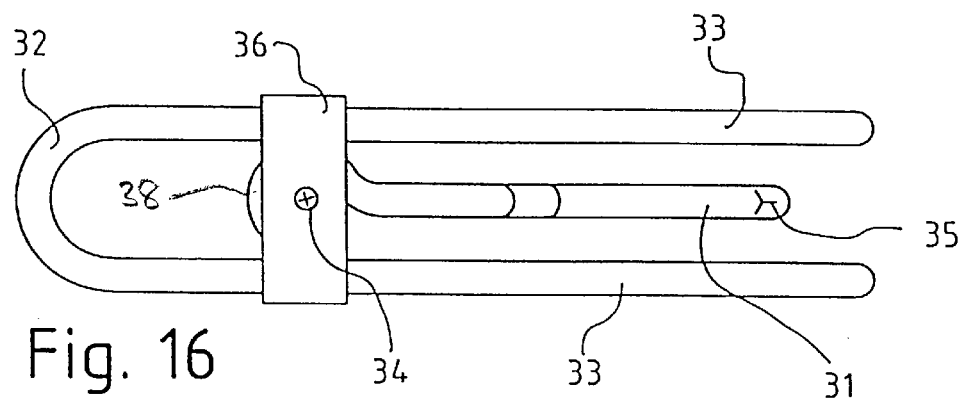
FIGS. 16–18 are top, side and end views, respectively, of a fifth embodiment of the invention.
Figure 17:
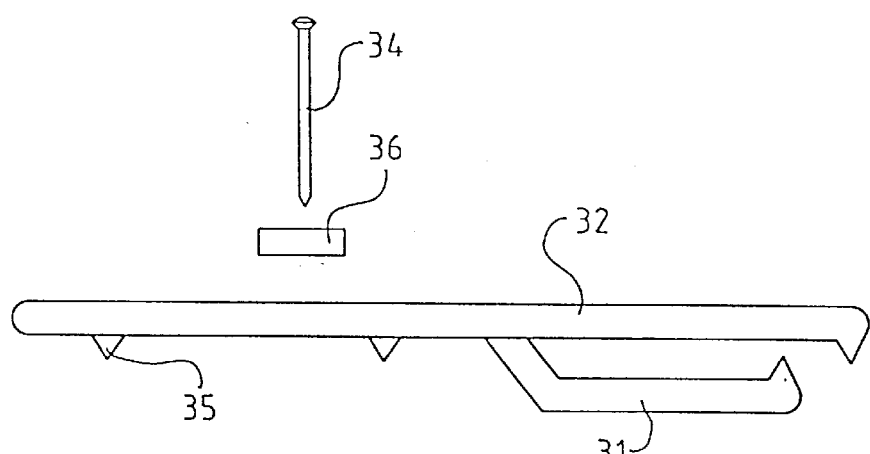
Figure 18:
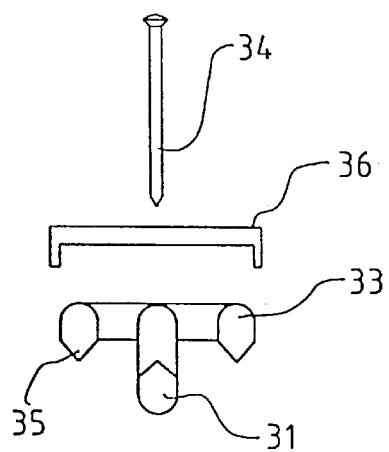

In FIGS. 16 to 18 a fourth embodiment of the fragment clamp according to the invention is shown. This embodiment resembles the previous embodiments in having a first linear part 31 and a second U-shaped part 32 with two legs 33. The first and second parts 31, 32 have projections 35 for engagement with bone cortex.

Figure 19:
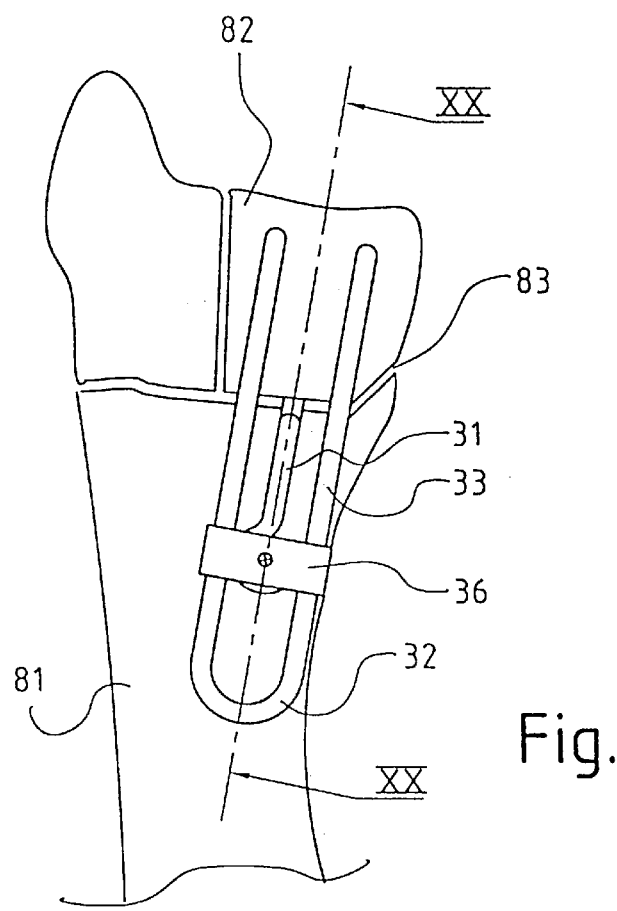
FIGS. 19–20 show application of the device of FIGS. 16–18 on a fracture, FIG. 20 being a cross-section taken on lines XX—XX in FIG. 19.
Figure 20:
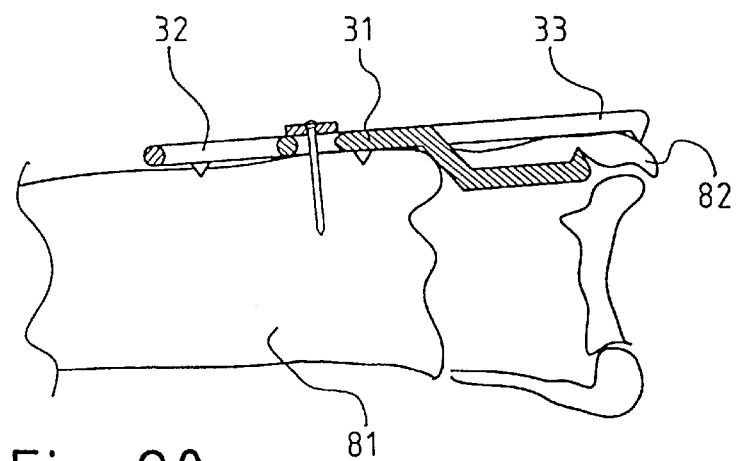

In this embodiment there is no cross tab on the first part 31, instead the bone fragment itself prevents the first part 31 from lifting up out of the second part 32. The proximal end of the first part 31 has a hook 38 which allows passage of a screw 34. The screw passes through a washer 36. This design is cheap and simple to manufacture. Application of this device on a bone is shown in FIGS. 19 and 20. FIG. 20 shows a cross-section taken along line XX—XX in FIG. 19.

As in the example shown in FIGS. 15a to 15f the first part 31 is first passed through the fracture 83, with or without a notch having been taken out. When the first part 31 is positioned, the second part 32 is placed with the legs 33 of the second part 32 on both sides of the first part 31 and with the distal ends of the legs 33 on the upper side of the fragment 82. Then the washer 36 is placed bridging the legs 33 of the second part 32. The washer 36 has a hole for receiving a bone screw 34 in alignment with the center of the hook 38 of the first part 31. Finally, the bone screw 34 secures the device on the stable bone 81 whereby the distal ends of the first and second parts 31, 32 sandwich the fragment 83. Thus, the first part 31 forms an intraosseous buttress and the second part 32 forms an extraosseous buttress.

Figure 30:
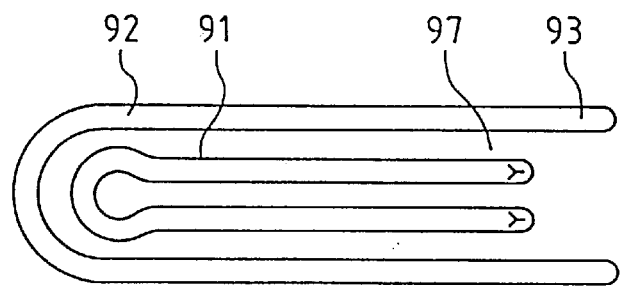
FIG. 30 is a top view of a further embodiment of the invention.
Figure 31:
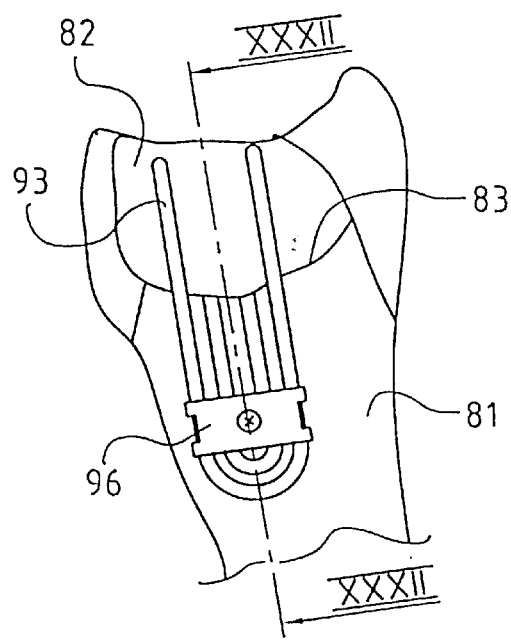
FIGS. 31–32 show the application of the device of FIG. 30 on a fracture, FIG. 32 being a cross-section taken on line XXXII—XXXII in FIG. 31.
Figure 32:
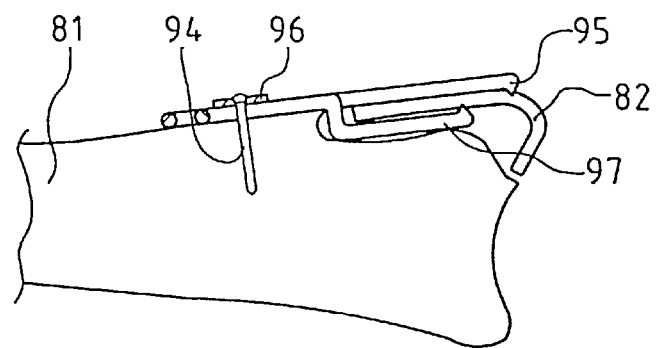

FIG. 30 shows a further embodiment of the fragment clamp according to the present invention. This embodiment has a first U-shaped part 91 with two legs 97 and a second U-shaped part 92 with two legs 93. Before placing the first part 91, the legs 97 of said part 91 are bent depending on the site of the fracture 83. Application of this device on a bone is shown in FIGS. 31 and 32. FIG. 32 shows a cross-section taken along the line XXXII—XXXII in FIG. 31. When applying the fragment clamp, the first part 91 is first passed through the fracture 83, with or without a the notch having been taken out. Then the second part 92 is placed with the legs 93 of said part 92 on both sides of the first part 91 and with the distal ends of the legs 93 on the upper side of the fragment 82. Both the first and second parts have pointed projections 95 for engagement with bone cortex. A washer 96 is then placed bridging the legs 93 of the second part 92. The washer 96 receives a bone screw 94, which secures the device on the stable bone 81. Thus, the distal ends of the first and second parts 91, 92 sandwich the fragment 83. The first part 91 forms an intraosseous buttress and the second part 92 forms an extraosseous buttress.

Some embodiments of the small fragment clamp allow the first part to be placed at a variable distance along the first component allowing central "fingers" extending as far as or farther than the outer fingers if desired or much shorter if desired. This feature allows the bend in the first part to be placed at the level of the fracture site where it would allow the first part to track up against the inner cortex of the bone fragment 82.

The above described embodiments are only examples of possible designs for a device according to the invention. In other embodiments the different parts of the embodiments shown are combined with different parts of the other embodiments. Thus, in further embodiments, both the first and second parts have U-shape in top view, the lengths of the legs of the U-shape differ, the number of arms on the intraosseous and the extraosseous side vary etc. In one embodiment there are two arms intraosseous and one arm extraosseous.

Figure 21:
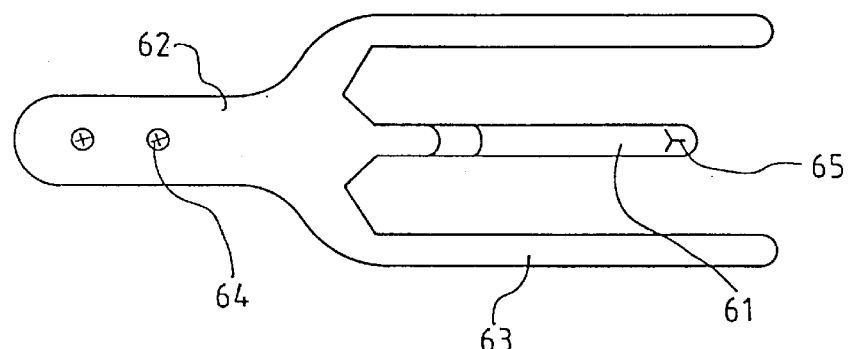
FIGS. 21–23 are top, side and end views, respectively, of a sixth embodiment of the invention.
Figure 22:
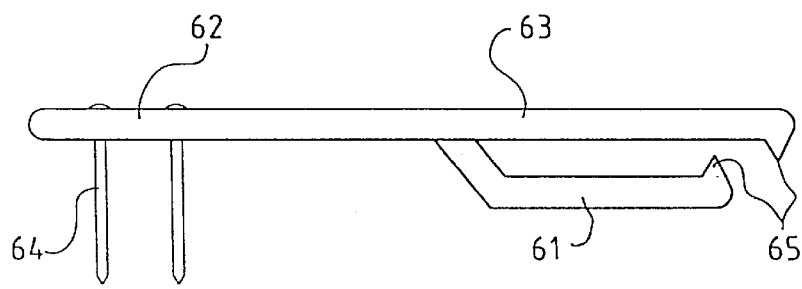
Figure 23:
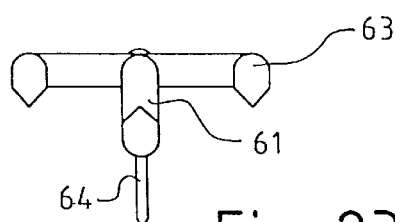

In the embodiment shown in FIGS. 21 to 23 the small fragment clamp is made in one piece. The clamp includes a base 62 and in side view a bent first part 61 for gripping and buttressing on the intraosseous side of a bone fragment. For gripping and buttressing on the extraosseous side of the bone fragment the clamp is provided with two straight legs 63, which are parallel with the first, bent part 61. Both the first part 61 and the two legs 63 have pointed projections 65 for engagement with cortex.

To secure the clamp to the stable bone, bone screws 64 are applied through holes in the base 62 of the clamp.

Figure 24:
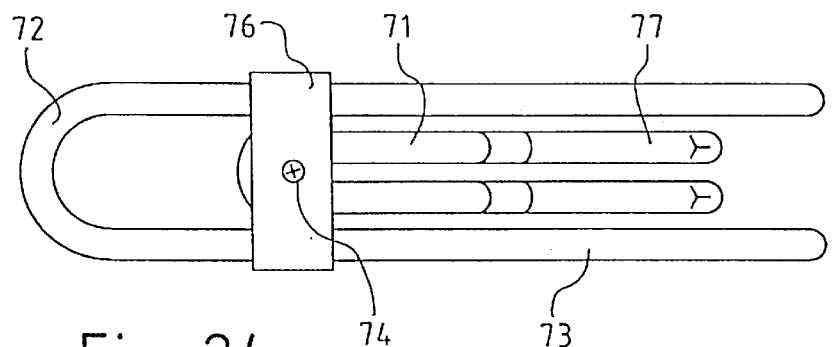
FIGS. 24–26 are top, side and end views, respectively, of a seventh embodiment of the invention.
Figure 25:
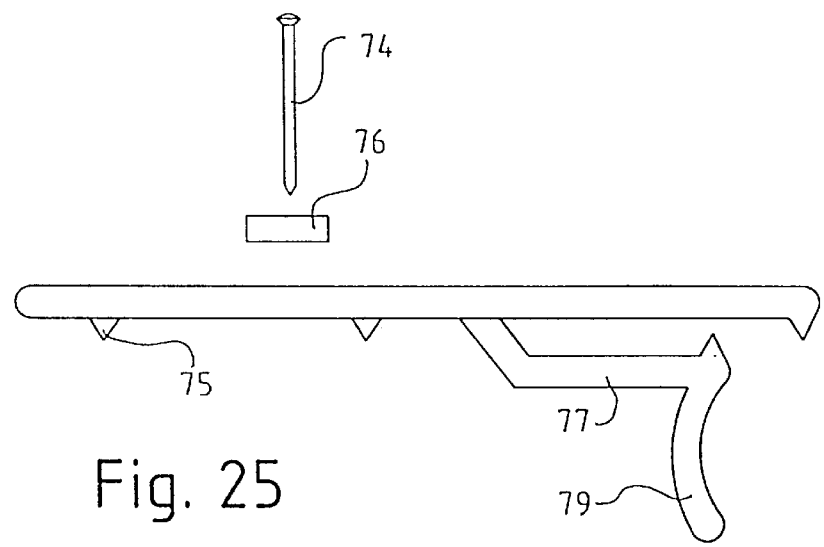
Figure 26:
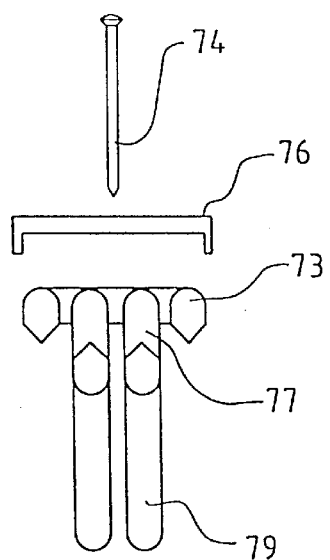

In FIGS. 24 to 26 a further embodiment according to the invention is shown, having both a clamping function and an intra-articular buttress function. The first part 71 has a general U-shape in top view with two legs 77 connected with a loop 78. In side view the legs 77 of the first part 71 show an intra-articular buttress 79 connected to the end of a bent section of the legs 77, which bent section cooperates with legs 73 of the second part 72 to grip a bone fragment.

To secure the clamp and the intra-articular buttress to the stable bone a bone screw 74 is used. The screw 74 passes through a washer 76, bridging the legs 73 of the second part 72, and passes through the loop 78 of the first part.

Figure 27:
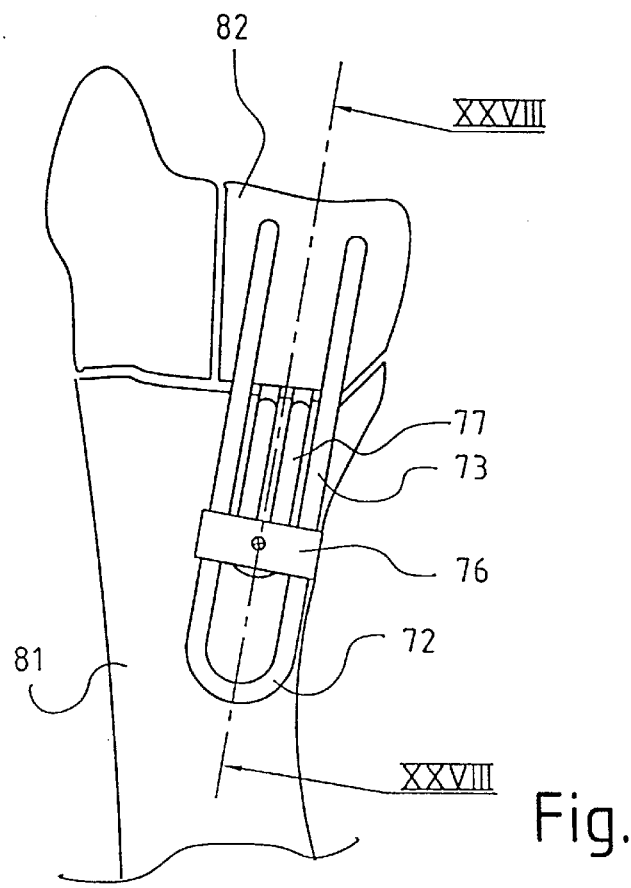
FIGS. 27–28 show application of the device of FIGS. 24–26 on a fracture, FIG. 28 being a cross-section taken on line XXVIII—XXVIII in FIG. 27.
Figure 28:
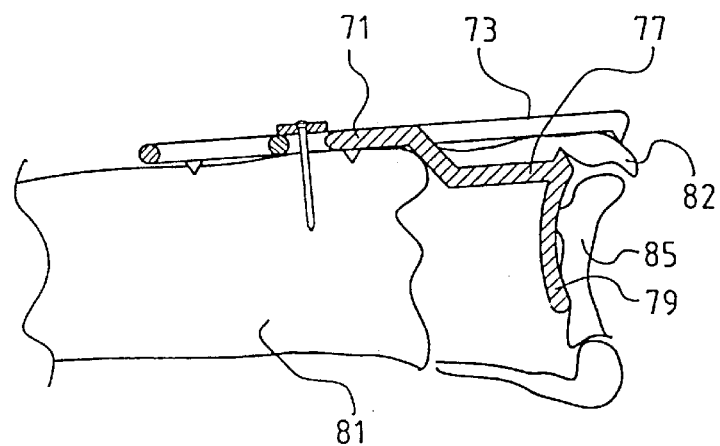

An example of application of the device of FIGS. 24 to 26 is shown in FIGS. 27 and 28. FIG. 28 shows a cross-section taken along the line XXVIII—XXVIII in FIG. 27. The first part 71 is first passed through the fracture, with or without a notch having been taken out, or through a hole made in the stable bone. To position the first part 71 with the intra-articular buttress 79 and the legs 77 in the desired positions it may be necessary to bend either part somewhat in one direction or other. When the first part 71 has been placed, the unstable fragment 82 to be gripped by the fragment clamp is placed on top of the legs 77 of the first part 71, which legs 77 function as a buttress for the fragment 82. Then the second part 72 and the washer 76 are placed. The washer 76 bridges the legs 73 of the second part 72 and has an aperture for receiving the bone screw 74 in alignment with the center of the loop 78 of the first part 71. Finally, the bone screw 74 secures the device on the stable bone 81 whereby the legs 73, 77 of the first and second parts sandwich the dorsal ulnar fragment 82 at the same time as the intra-articular buttress 79 of the first part 71 buttresses an intra-articular fragment 85.

Figure 29:
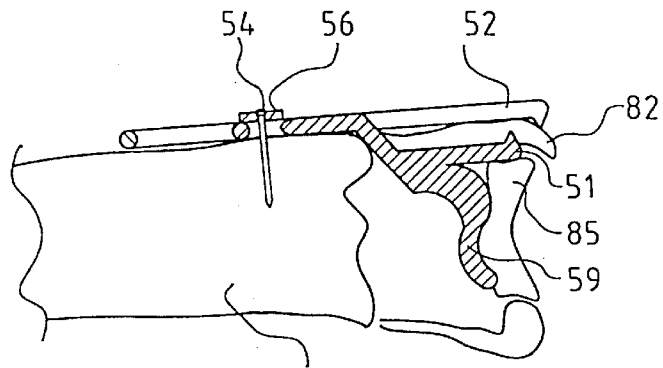
FIG. 29 shows in sectional view application of a combined device according to the invention on a fracture.

In FIG. 29 a further device is shown applied on a fracture, having both a clamping function and an intra-articular buttress function. In this embodiment the first part 51 grips on the lower side of a first fragment 82 at the same time as an intra-articular buttress 59 of the first part 51 force a second fragment 85 against the opposite side of the joint. The second part 52 grips on the upper side of the first fragment 82. This device is secured to the stable bone 81 with a bone screw 54 passing through a washer 56. As in the previous embodiments pointed projections are used to stabilize the device further.

In some embodiments there are no pointed projections and in other embodiments there are one or more raised areas for contact with the bone. In a further embodiment (not shown) a two piece first part is used, which can be coupled during insertion at the site of bone penetration.

The method of placement of the device according to the invention sometimes require the removal of a small notch of bone to allow passage of the first part. The first part is flexible enough to allow its removal simply by sliding this member proximally at the time of device removal.

Figure 33:
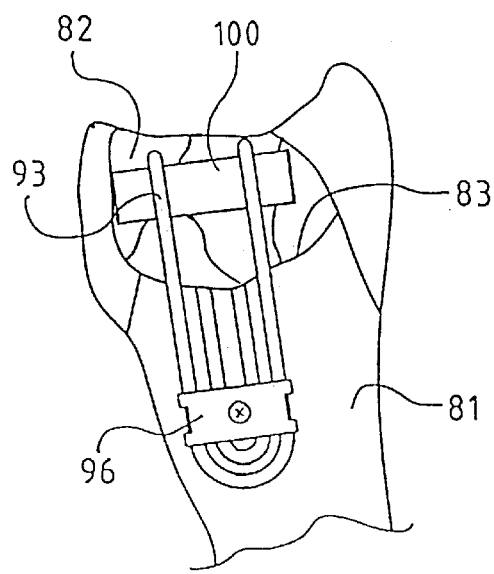
FIG. 33 shows the application of an optional plate.

In cases where the patient has a severe fragmentation and possibly soft bone (osteoporosis), there is a risk that the legs of the second part find a crack between the fragments and fall within the crack. To avoid this risk, a small plate 100 is placed between the extraosseous surface of the fragments and the legs 93 of the second part 92. In this way the load of the clamp is spread over a wider area. Although the plate 100 is shown in FIG. 33 in connection with the device according to FIG. 30, a person skilled in the art realizes that said plate could be used with any fragment clamp according to the invention.

Figure 34:
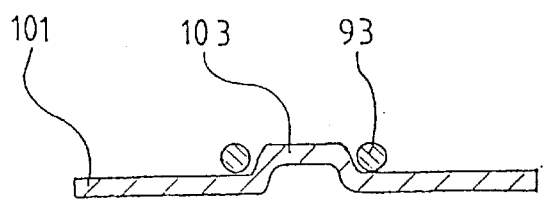
FIGS. 34–35 show different embodiments of the plate according to FIG. 33 in sectional view.
Figure 35:
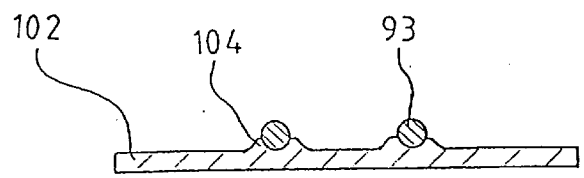

In its most simple embodiment, the plate 100 is a simple straight plate. In further embodiments the plate is furnished with means 103, 104 to constrain the plate from migrating. Two examples of this are shown in cross-section and enlarged in FIGS. 34 and 35. The plate 101 according to FIG. 34 has a raised area 103 between the legs 93 of the second part of the fragment clamp. The plate 102 according to FIG. 35 is furnished with two seats 104 for receiving the legs 93 of the upper part of the fragment clamp. In a further embodiment (not shown) the plate has two slots at the distal edge to allow the legs 93 near the tip to pass through to the bone. In still a further embodiment (not shown) two small holes are placed near the distal edge of the plate to allow the pointed projections of the outer component to gain some purchase on the plate. Thus, the plate is constrained from migrating by cooperation between the legs 93 of the clamp and a constraining means 103, 104 of the plate 101, 102. If needed, the plate 100, 101, 102 is bent to conform to the dorsal surface As an option (not shown) the legs of both the first part and the second part are delivered straight i.e. not bent in side view. In this case the legs of the first part are custom bent depending on the fracture site, the size of the fragments etc. before application by the surgeon. In this embodiment it is possible to cut the ends of the legs to desired lengths and optionally bend in a point at the end if desired.

The first and second parts of this device are preferably made of wires having a diameter between 0.010" to 0.250". In one embodiment 0.045" wire is used and in a second embodiment 0.054" wire is used. In other embodiments, the first and second parts are not made of wires, in which case the cross section of the legs of each part has the shape of a bar, plate, triangle, hexagonal or the like.

The invention also contemplates using the U-shape second part on its own as a separate unit for fixation of bone fragments or grafts to an adjacent stable bone. Thus, for example, the U-shape component 2 in FIGS. 6–8 can be used alone to fix one or more bone fragments to an adjacent stable bone without using component 1. Although a clamping function would be eliminated by the absence of component 1, the fixation and buttressing effect would be preserved. FIGS. 19, 20; 27, 28; 31, 32 illustrate the buttressing and fixation function which would be provided by the U-shape component alone.

Thus, in its broadest concept, the device of the invention is constituted by the U-shaped part 2 alone, formed of wire, and having a U-portion with legs 3 provided with pointed projections 5 at their distal ends. The U-shaped part 2 has a low profile, i.e. the wire is disposed in a common plane, and the pointed projections 5 extend at an angle from the common plane (90° in FIG. 7). The projections 5 restrict translational movement of the bone fragments and bone grafts in which they are engaged.

Figure 36:
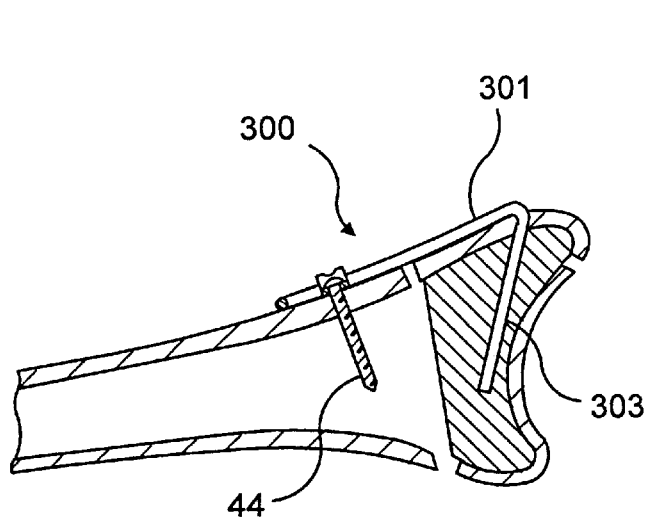
FIG. 36 is a side, sectional view of a further embodiment of the invention showing fixation of a bone fragment.

In the embodiment shown in FIG. 36, the U-shaped component is shown at 300 and includes the U-portion 301 and legs 302 extending therefrom. At the distal ends of the legs 302, projections 303 are formed by bending the ends of the legs out of the plane of the U-shaped component. The bent legs 302 project a much greater distance out of the plane of the U-shaped component than do the pointed projections 5 in FIG. 7.

Figure 38:
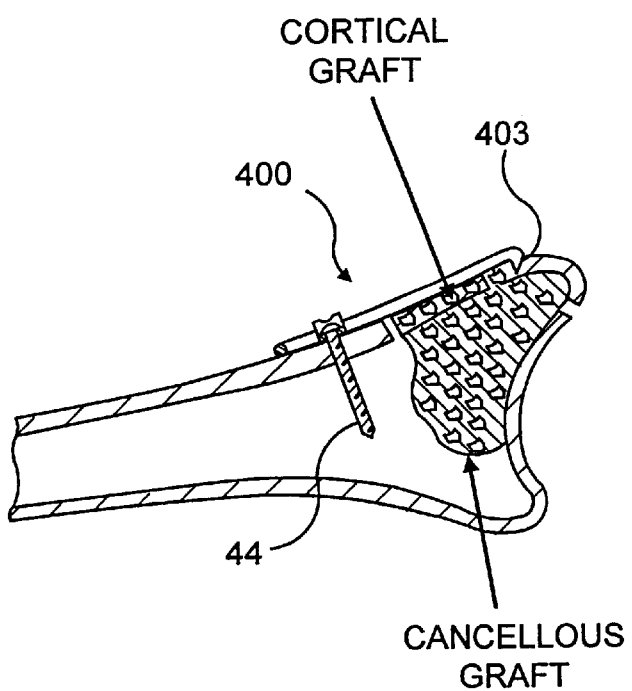
FIG. 38 is a side sectional view of another embodiment showing fixation of a bone graft.
Figure 39:
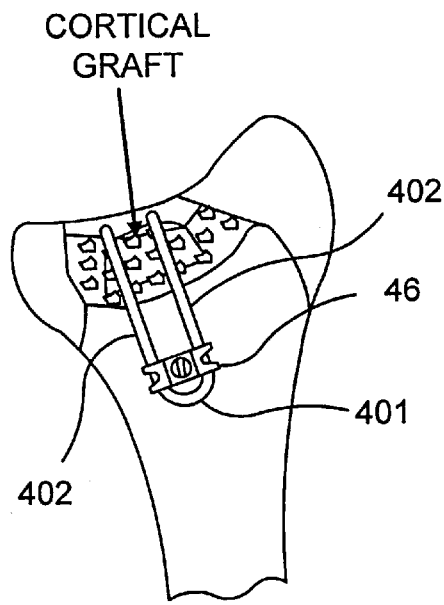
FIG. 39 is a top view of the embodiment of FIG. 38.

FIG. 36 shows the U-shaped component installed to fix a fracture site 304. The component is installed by first drilling two small holes into the bone fragment to receive the projections 303. If the component is utilized to stabilize a bone graft, the holes through the cortex will be drilled into the graft in a manner which will become evident when describing FIGS. 38 and 39. The projections 303 are hammered into the holes drilled in the cortex and bone fragment. The U-shaped component is secured to the stable bone by washer 46 and bone screw 44. It is also possible to apply a contraction force across the fracture site (or the graft joint). This is achieved by applying a pulling force on the U-shaped component after the projections 303 have been seated in the drilled holes and while installing bone screw 44.

When the device of the invention utilized for stabilizing bone grafts, it is not restricted to free grafts, but can be used with partially or completely devascularized bone fragments that are essentially acting in the capacity as bone grafts, or even in the general case of any bone fragment, whether produced locally by the fracture itself, or brought in from a remote site as a free bone graft.

Figure 37:
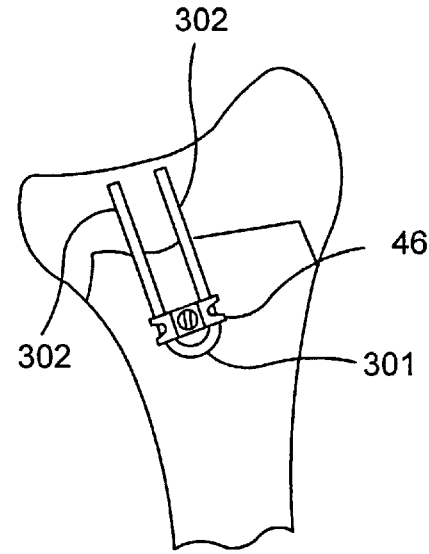
FIG. 37 is a top view of the embodiment in FIG. 36.

FIGS; 38 and 39 show the device used for fixation of a cortical bone graft and a cancellous bone graft. The device comprises a U-shaped component 400 having a U-shaped bend 401 and legs 402 extending therefrom. At the distal ends of the legs 402 are pointed projections 403 to restrict movement of the bone graft. Instead of the pointed projections 403, the component 400 can be provided with bent legs as in FIGS. 36 to engage the cancellous graft. As in FIGS. 36 and 37, the component is secured at its end opposite the projections 403 by washer 46 and bone screw 44.

In one further embodiment (not shown) at least one of the legs of the first and/or second part is bent or angled in top view. The above bent or curved sections are predominantly arranged at the tip of the legs, but in some embodiments the entire legs (or leg) has a bent or angled shape as viewed from above.

The expressions lower, upper etc. as used in the description are used for convenience and only refers to the drawings specifically referred to, without any limitations to the actual design of the products.

The above detailed description has referred to but a limited number of embodiments of the present invention, but it will be readily perceived by a person skilled in the art that the present invention encompasses a large number of embodiments without departing from the spirit and scope of the appended claims.

What is claimed is:

1. An implantable surgical buttressing means for fixation of one or more bone fragments or grafts to an adjacent stable bone, said buttressing means comprising a U-shaped wire including a U portion and two legs extending from said U portion, said buttressing means being securable at one end thereof, by a fixation means, to a stable bone, at least one of said legs of said U-shaped wire including projection means for penetrating the surface of the bone fragment or graft to provide translational constraint of the fragment or graft.

2. A surgical buttressing means as claimed in claim 1, wherein said projection means is formed by a bend in said at least one of said legs.

3. A surgical buttressing means as claimed in claim 2, wherein said U-shaped wire is disposed substantially in a plane and said projection means extends from said plane.

4. A surgical buttressing means as claimed in claim 3, wherein both of said legs include a respective said bend and corresponding said projection means.

5. A surgical buttressing means as claimed in claim 1, wherein said projection means comprises a pointed projection protruding from a distal end of said at least one of said legs at right angles thereto.

6. A surgical buttressing means as claimed in claim 5, wherein one said pointed projection is provided at the distal end of each said leg of said U-shaped wire.

7. A surgical buttressing means as claimed in claim 1, wherein said U-shaped wire is disposed substantially in a plane and said projection means extends from said plane.

8. A surgical buttressing means as claimed in claim 1, wherein said fixation means comprises a bone screw which is insertable into the stable bone to apply a rearwardly directed force on said at least one leg and produce a contraction force across a fracture site or bone graft.

9. A surgical buttressing means as claimed in claim 8, wherein said projection means is formed by a bend in each of said legs to provide projections extending out from a plane containing the U-shaped wire, said projections being adapted to provide the translational constraint of the fragment or graft, the bends in the legs enabling the buttressing means to apply a rearwardly directed force on said legs for producing a contraction force across a fracture site or bone graft.

* * * * *